US005573539A

United States Patent [19]

Alexander

[11] Patent Number: 5,573,539

[45] Date of Patent: *Nov. 12, 1996

[54] DEVICE FOR ASSISTING IN THE BIRTH OF LIVESTOCK

[75] Inventor: Gary E. Alexander, Baton Rouge, La.

[73] Assignee: Medisys Technologies, Inc., Baton Rouge, La.

[ * ] Notice: The term of this patent shall not extend beyond the expiration date of Pat. No. 5,318,573.

[21] Appl. No.: 254,120

[22] Filed: Jun. 6, 1994

[51] Int. Cl.[6] .................................................. A61B 17/42

[52] U.S. Cl. .......................... 606/122; 606/119; 606/121

[58] Field of Search .................................... 606/119–124

[56] References Cited

U.S. PATENT DOCUMENTS

| | | | |
|---|---|---|---|
| 3,183,911 | 5/1965 | Anglemyer . | |
| 3,550,595 | 12/1970 | Laufe . | |
| 3,605,748 | 9/1971 | Salinas-Benavides . | |
| 3,643,664 | 2/1972 | McMillan . | |
| 3,665,925 | 5/1972 | Dersookian . | |
| 3,785,381 | 1/1974 | Lower . | |
| 3,789,849 | 2/1974 | Laufe et al. . | |
| 3,794,044 | 2/1974 | Vennard . | |
| 3,955,582 | 5/1976 | Pierce . | |
| 4,502,486 | 3/1985 | Weiland . | |
| 4,875,482 | 10/1989 | Hariri et al. | 606/122 |
| 5,122,148 | 6/1992 | Alexander | 606/122 |
| 5,217,467 | 6/1993 | Alexander | 606/122 |
| 5,318,573 | 6/1994 | Alexander | 606/122 |

*Primary Examiner*—Angela D. Sykes
*Assistant Examiner*—Michael Peffley
*Attorney, Agent, or Firm*—Roy, Kiesel & Tucker

[57] ABSTRACT

A device for assisting in the birth of livestock is disclosed. The device, known as a fetlock puller, is elongated, has at least one end open, and is sized so that the one open end will fit over the fetlock of an unborn animal fetus. The fetlock is the large bulge on an animal's foreleg just above the hoof. The fetlock puller is constructed of braid material which will cause the device to axially grip the foreleg as traction is applied. The device can also be used to suspend a newborn animal and hook it to a scale so it can be weighed.

9 Claims, 7 Drawing Sheets

DEVICE FOR ASSISTING IN THE BIRTH OF LIVESTOCK

BACKGROUND OF THE INVENTION

1. Field of the Invention

This invention relates generally to veterinary obstetric devices. More particularly, but not by way of limitation, this invention relates to devices useful in removing the animal fetus during vaginal delivery.

2. Prior Art

Cattle, horses and sheep normally deliver their young vaginally. Complications arise in livestock births just as complications arise in the births of humans. For example, in approximately 10–25% of the births of calves, traction is required. One can expect a similar traction requirement in the births of foals and lambs. Traction is the application of force to the presenting parts of the animal fetus in order to supplement or replace the natural maternal forces in removing the animal fetus from the uterus of the animal mother. Presenting parts are those parts of the animal fetus nearest the vaginal opening of the animal mother.

The following description of livestock delivery is intended as generic to bovine (cattle), equine (horses), and ovine (sheep) deliveries. In a normal presentation (i.e. positioning) of the fetus, the presenting parts are the forelegs (i.e. front legs) and head of the animal fetus. The forelegs appear first, heels down, with one foreleg slightly in front of the other; and the head is between the forelegs. In human deliveries, the mother experiences the greatest difficulty in passing the head through the birth canal. In livestock deliveries, the mother animal typically experiences the greatest difficulty in passing the shoulders through the birth canal because the shoulders are the widest part of the animal fetus's body.

If the animal mother appears to be straining but not progressing in expelling the animal fetus, traction may be required. The prior art reveals several robust, if not crude, traction implements including chains, cords, snares, hooks, tongs, cutters, and winch-type or rachet-type mechanical extractors. All of these devices are used to apply traction force to the forelegs or the head, or both, of the fetus.

The most common device used for applying traction to the forelegs is the Moore's chain. A Moore's chain typically consists of a length of steel chain with a large closed steel ring connected to the last link at each end of the chain. Each of these closed steel rings is of sufficient size to allow a portion of the chain to be wrapped around the animal fetus's foreleg and passed back through the ring. The chain operates on the same principle as a dog choker-chain. When a dog choker-chain is pulled along its length, the loop around the dog's neck is tightened. In the use of a Moore's chain, each end of the chain is used to form a loop around each foreleg of the fetus. A handle or a mechanical traction device is attached to the approximate midpoint of the chain and traction force is applied, thereby tightening each loop around the two forelegs of the animal fetus and pulling the forelegs out of the mother animal. There are other devices, similar to the Moore's chain, which work using the choker-chain concept but employ cord, rope, or cable instead of chain.

Normally when traction is indicated it is applied simultaneously to the forelegs and the head; although traction may initially be applied to the forelegs alone until the head becomes accessible. Devices for applying traction forces to the head consist of various cables, cords, or ropes which are looped around the head. One commonly used device, known as a cable head puller, comprises a steel wire cable which is looped around the animal fetus's head just below the ears. After looping around the animal fetus's head, the two ends of the cable pass through a metal locking slide which holds the loop tightly around the animal fetus's head. The metal locking slide works in a way similar to a western-style string tie. The metal locking slide also has a portion which engages the teeth of the animal fetus. The two cable strands pass through the metal locking slide and terminate, joined together, in a yoke at the end of the cable. The yoke can be connected to a handle for applying human traction or the yoke can be connected to a mechanical traction device. Traction can be applied to the cable head puller alone or the cable head puller and the Moore's chain can both be connected to a handle or a mechanical traction device.

The design emphasis of the Moore's chain and devices similar to it has been toward ensuring an effective grip on the animal fetus. Little consideration appears to have been given toward minimizing the translation of the pulling and gripping forces into blunt trauma of the animal fetus and the animal mother. An additional shortcoming of the Moore's chain is that the foreleg is turned in the birth canal because the chain loops exert forces not aligned with the axis of the birth canal. This misdirected force causes an even wider cross-section of the presenting parts of the animal fetus in an animal mother who is already unable to naturally expel the animal fetus.

When using Moore's chains, the likelihood of injury is high because of the great forces used in traction. One skilled in the art will know that the force of four average men will usually be required to extract the animal fetus in a traction-assisted birth. Accordingly, fetal and maternal injuries are fairly common in traction-assisted births. The injuries can result in death of the animal fetus or animal mother, fetal limb loss, or fetal treatment for secondary infections resulting from injuries incurred in delivery.

Regardless of the extent of the injury, the net result for the cattle, horse, or sheep rancher is ranch hand time lost on treatment of birth injuries or secondary complications. In many cases veterinary intervention may be required, which will cost the rancher additional money. The need for a veterinary traction device which reduces trauma is motivated not only by cost savings, but also by compassion for the animal fetus and the animal mother.

The Moore's chain can also cause human as well as animal injury. As mentioned earlier, it is known in the art that the force of four average men will be necessary to replace the maternal forces. Because of the force required, in cases in which mechanical traction cannot be used or a mechanical traction device is not available, more than one assistant is involved. It is simply not possible for four assistants to fit their hands on the handle. Therefore, it is common for the assistants to grab a portion of the Moore's chain near the point where the Moore's chain is connected to the handle. Often the assistants' hands are pinched in the chains or the assistants are limited in the amount of force they can apply because of the pain suffered from grabbing a steel chain.

The Moore's chain and other similar devices which use the choker-chain concept have at least one other significant drawback. Such devices remain securely wrapped about the forelegs only when traction force is applied. If the traction force is interrupted for any reason, the gripping force is also interrupted. The loops on the forelegs can then slip to an improper position or come off completely, requiring a human assistant to reposition the chain.

This failure to securely hold the foreleg when slack is also significant when the choker-chain type devices are put to their secondary use, weighing the newborn animal. To weigh the newborn animal, one Moore's chain is looped around the newborn animal's forelegs, and a second Moore's chain is looped around the hindlegs (i.e. back legs). The chains are gathered together at their approximate midpoints and hooked to a scale so that the newborn animal is suspended in mid-air.

Those skilled in the art will know that the newborn animal is usually uncooperative in this venture. Significant ranch hand time is wasted subduing the newborn animal long enough to hook up the Moore's chain or a similar device. With the slightest interruption in the pulling force, the loops on the forelegs and hindlegs loosen and an uncooperative newborn animal can extract one or more of its legs from the chains.

Examples of current veterinary devices include U.S. Pat. No. 3,643,664 entitled "Dual-Pull Veterinary Fetal Extractor" issued on Feb. 22, 1972 to Robert L. McMillan; U.S. Pat. No. 3,183,911 entitled "Fetal Extractor" issued on May 18, 1965 to Alfred A. Anglemyer; U.S. Pat. No. 3,955,582 entitled "Obstetrical Tool For Animals" issued on May 11, 1976 to Richard C. Pierce; and U.S. Pat. No. 4,502,486 entitled "Device For Veterinary Obstetrical Delivery" issued on Mar. 5, 1985 to Werner Weiland. Human traction devices include U.S. Pat. No. 3,550,595 entitled "Obstetrical Forceps" and issued on Dec. 29, 1970 to Leonard E. Laufe; U.S. Pat. No. 3,605,748 entitled "Obstetrical Forceps" and issued on Sep. 20, 1971 to Hector Salinas-Benavides; U.S. Pat. No. 3,665,925 entitled "Obstetrical Forceps" and issued on May 30, 1972 to Hamo M. Dersookian; U.S. Pat. No. 3,785,381 entitled "Pressure Sensing Obstetrical Forceps" and issued on Jan. 15, 1974 to Brenton R. Lower et al; U.S. Pat. No. 3,789,849 entitled "Obstetrical Forceps" and issued on Feb. 5, 1974 to Leonard E. Laufe et al; U.S. Pat. No. 3,794,044 entitled "Delivery Forceps" and issued on Feb. 26, 1974 to William O. Vennard; U.S. Pat. No. 5,122,148 entitled "Device For Assisting Childbirth" issued on Jun. 16, 1992 to Gary E. Alexander; and U.S. Pat. No. 5,217,467 entitled "Device For Assisting Childbirth" issued on Jun. 8, 1993 to Gary E. Alexander.

OBJECTS OF THE INVENTION

It is an object of the present invention to provide a device for the traction-assisted birth of livestock which will significantly reduce the likelihood of injury to the animal fetus and the animal mother.

Another object of this invention is to provide a device which will hold and pull the legs of the animal fetus or newborn animal without slipping off and without allowing the animal to extricate itself from the device when the traction force is lessened.

Another object of this invention is to provide a device for pulling the animal fetus's forelegs which will increase the gripping force around the forelegs as the traction force is increased.

It is also an object of this invention to provide a device for gripping the animal fetus's forelegs which is compatible for use with existing cable head pullers and for use with human or mechanical traction devices.

SUMMARY OF THE INVENTION

The present invention, a fetlock puller, is an elongated member which is sized to fit over the average foreleg of the particular type of livestock being extracted. The device has an open first end and a second end connected by a passageway. In one embodiment the open first end includes a means for tightening the open end around the foreleg. In another embodiment, the fetlock puller has an attaching means at the second end for connecting the fetlock puller or to another fetlock puller or to a human or mechanical traction device. The device is constructed so that as traction force is applied, the fetlock puller will axially grip the foreleg along the entire length in which the fetlock puller and the foreleg are in contact.

It is a feature of this invention that great traction force may applied to the forelegs of the animal fetus while minimizing the trauma to the forelegs.

It is a further feature of this invention that the device securely holds the forelegs of the animal fetus and the animal fetus cannot extricate its forelegs from the device, even when the traction force is interrupted.

It is a further feature of this invention that the device increases the gripping force around the forelegs of the animal fetus as the traction force is increased.

It is a further feature of this invention that the device is compatible for use with existing cable head pullers and mechanical traction devices.

It is a further feature of this invention that the force applied to the forelegs is aligned with the axis of the birth canal so that the cross-section of the presenting part of the animal fetus is minimized.

It is an advantage of this invention that more than one operator can grab the device and exert their maximum strength without pain or risk of injury to the operators of the device.

It is an advantage of this invention that the device may also be used to weigh an animal.

These and other objects, features, and advantages of this invention will be apparent from the following descriptions of the invention.

DETAILED DESCRIPTION OF THE PREFERRED EMBODIMENTS

Figure 1:
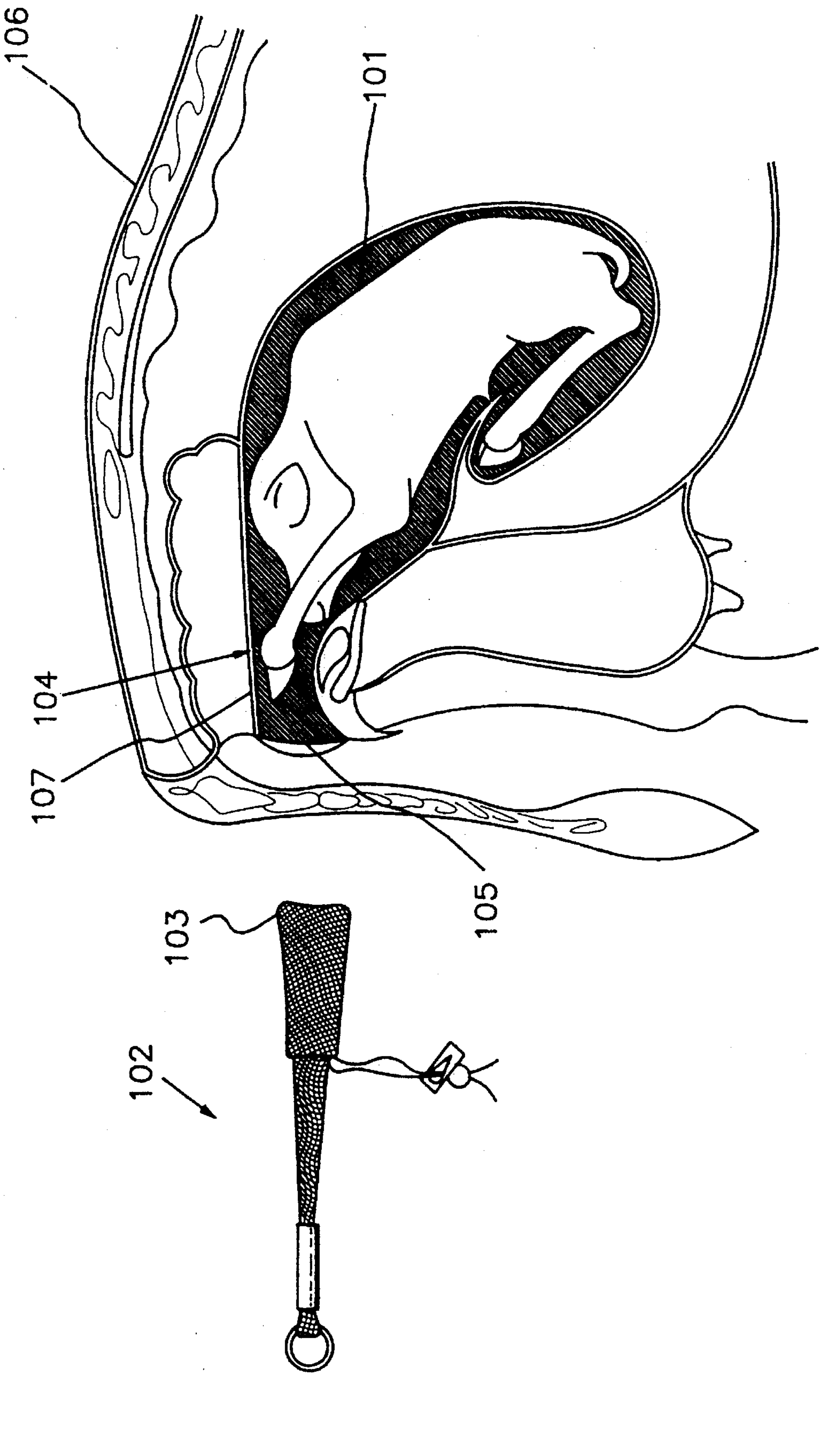
FIG. 1 is a sectional view of a calf fetus inside the mother cow in a normal presentation. The single device embodiment of the invention is depicted, and the device has been cocked, ready for placement on a foreleg of the animal fetus.

Referring to FIG. 1, animal fetus 101 is shown in the normal presentation for vaginal delivery. The device, hereinafter called a fetlock puller, is shown just outside of animal mother 106, and the embodiment of the device shown is that of a single fetlock puller, generally indicated by the numeral 102. Single fetlock puller 102 is shown ready for use in the cocked position, it which it has been folded partially inside out. As will be discussed in greater detail later in this specification, the operator will remove foreleg 104 from birth canal 107 through vaginal opening 105 of animal mother 106, place folded edge 103 over foreleg 104, and unfold single fetlock puller 102.

Figure 2:
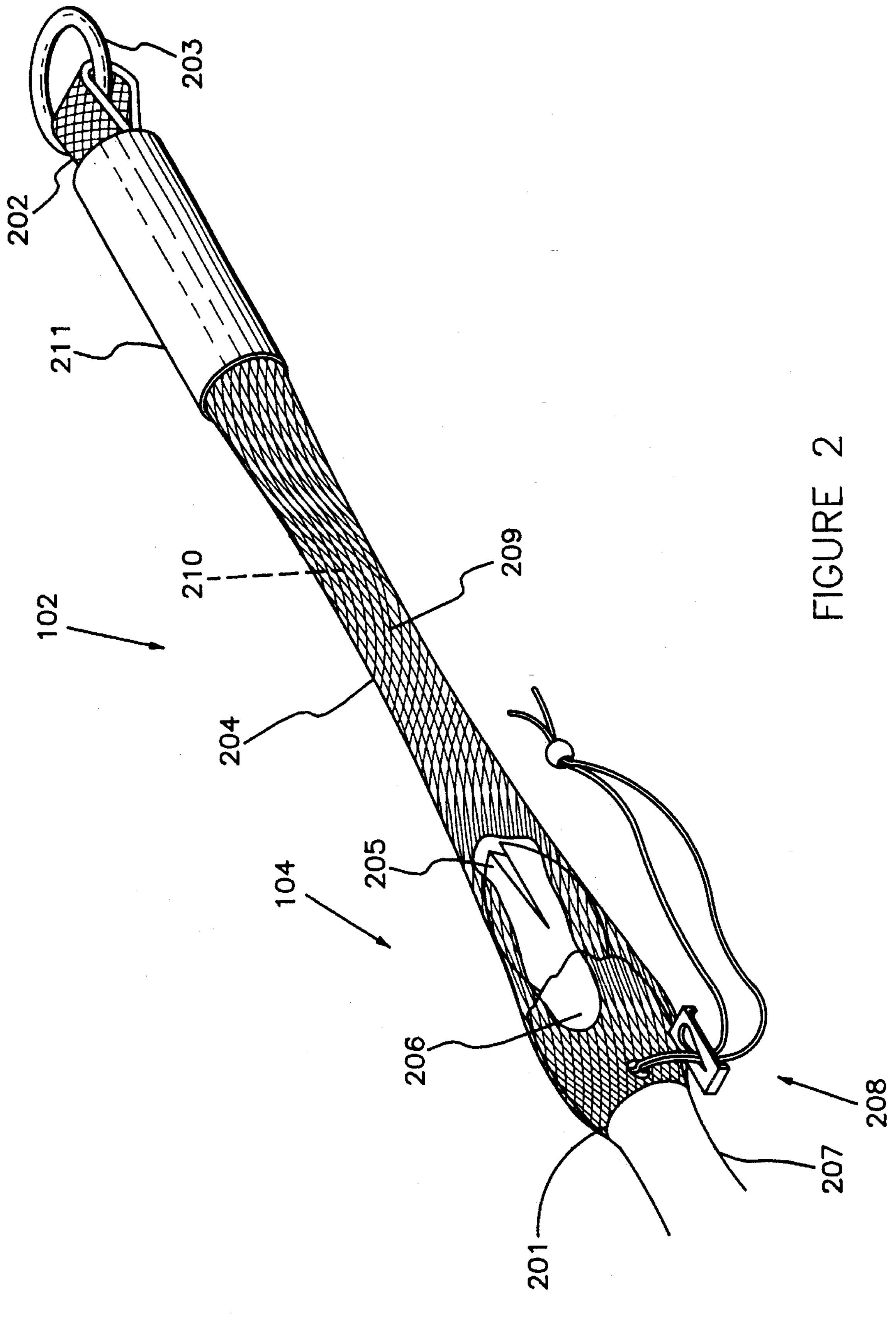
FIG. 2 is a perspective view of the single device embodiment of the invention placed over the foreleg of an unborn animal fetus.

Referring now to FIG. 2, a perspective view of single fetlock puller 102 placed over foreleg 104 is shown. Single fetlock puller 102 is an elongated member 204 and has open first end 201 and second end 202 connected by passageway 210. In the embodiment shown, second end 202 is closed and terminates in attaching means 203. However second end 202 could be open, giving single fetlock puller 102 a tube-like shape.

Attaching means 203 is connected to second end 202 by passing the material of elongated member 204 through attaching means 203, folding the material back onto itself, and joining the folded portion to second end 202 with stitching and pliable shrink-wrap 211. Other means for connecting attaching means 203 to second end 202 could include using only stitching or only shrink-wrap, or stapling the folded portion to second end 202, or using any other conventional means or methods to connect attaching means 203 to second end 202. A metal ring is depicted as attaching means 203 but a snap ring, swivel ring, rope loop, or any other means for connecting second end 202 to an attaching means 203 of another fetlock puller or a traction device could be used.

FIG. 2 also depicts the key anatomical features of foreleg 104. Fetlock 206 is the large bulge just above hoof 205 and just below upper foreleg portion 207. When single fetlock puller 102 is unfolded and optimally positioned, hoof 205 and fetlock 206 are completely engulfed in elongated member 204 and open first end 201 is around upper foreleg portion 207. Open first end 201 and passageway 210 are sized so that elongated member 204 will just fit over foreleg 104 of animal fetus 101.

Elongated member 204 is constructed of braid material 209 which will axially grip foreleg 104 when single fetlock puller 102 is pulled from second end 202. Elongated member 204 and braid material 209 are constructed so that the axial gripping forces will increase as the traction force applied at second end 202 is applied. Cooperating with open first end 201 is tightening means 208 for tightening open first end 201 around upper foreleg portion 207. Tightening means 208 will decrease the size of the opening at open first end 201 so that axial gripping will initiate when elongated member 204 is pulled from second end 202.

Figure 5:
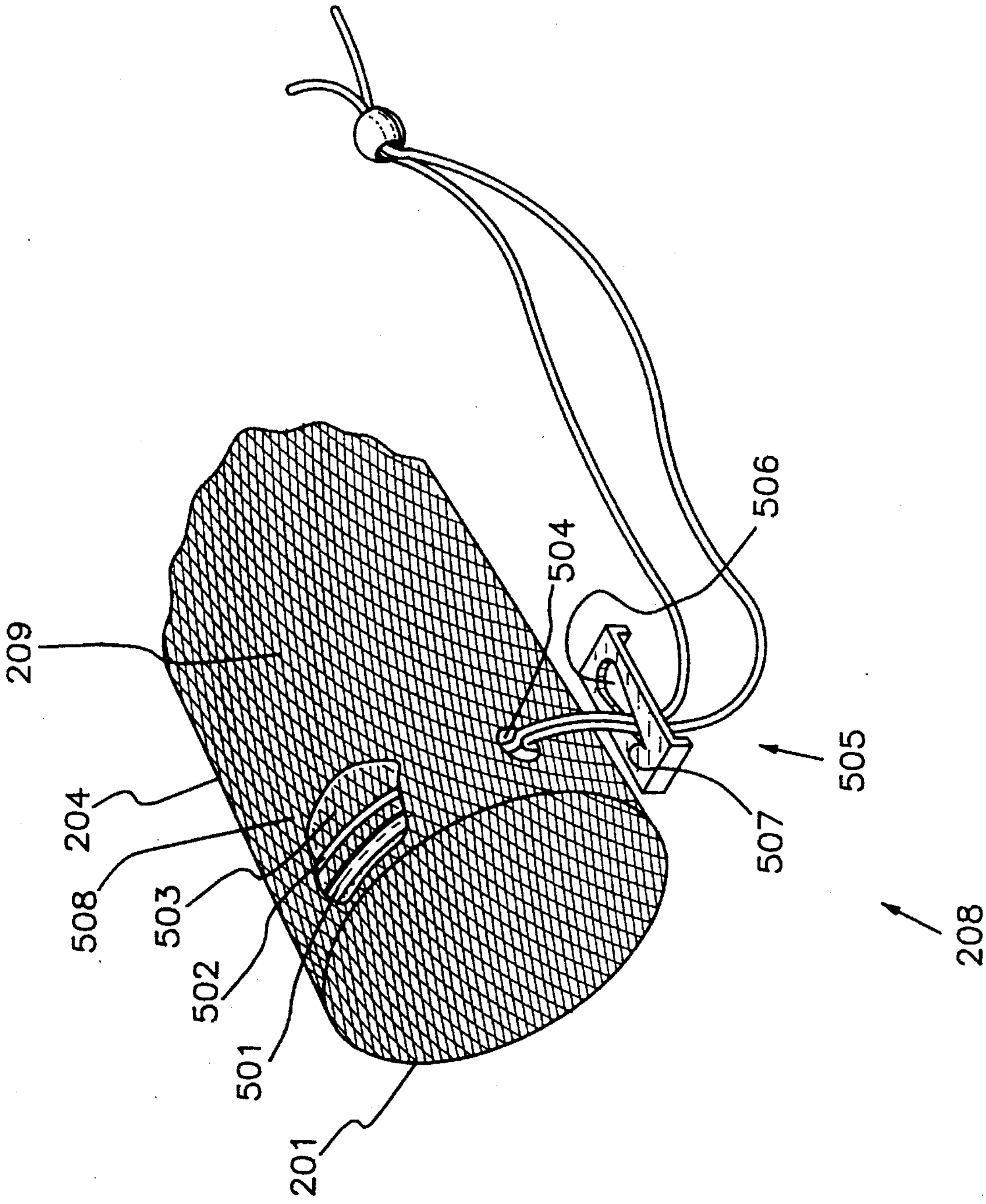
FIG. 5 is a enlarged perspective view of the open end of a single device embodiment of the invention. A portion of the top layer of the device has been cut away.

FIG. 5 is an enlarged perspective view of open first end 201 of elongated member 204. The cut-away portion shows that elongated member 204 will have inner layer 503 and outer layer 508. The preferred way to obtain inner layer 503 and outer layer 508 is to extrude a continuous cylindrical member and then fold the cylindrical member so that the folded material extends all the way back to second end 202, thereby forming inner layer 503 and outer layer 508. One could terminate braid material 209 by cutting braid material 209 at open first end 201 and sewing or binding the fibers together. However, it is preferred to terminate braid material 209 by folding braid material 209 to form a two-layered member because this embodiment will enhance the axial gripping aspects of braid material 209 and will be easier to manufacture.

Figure 7:
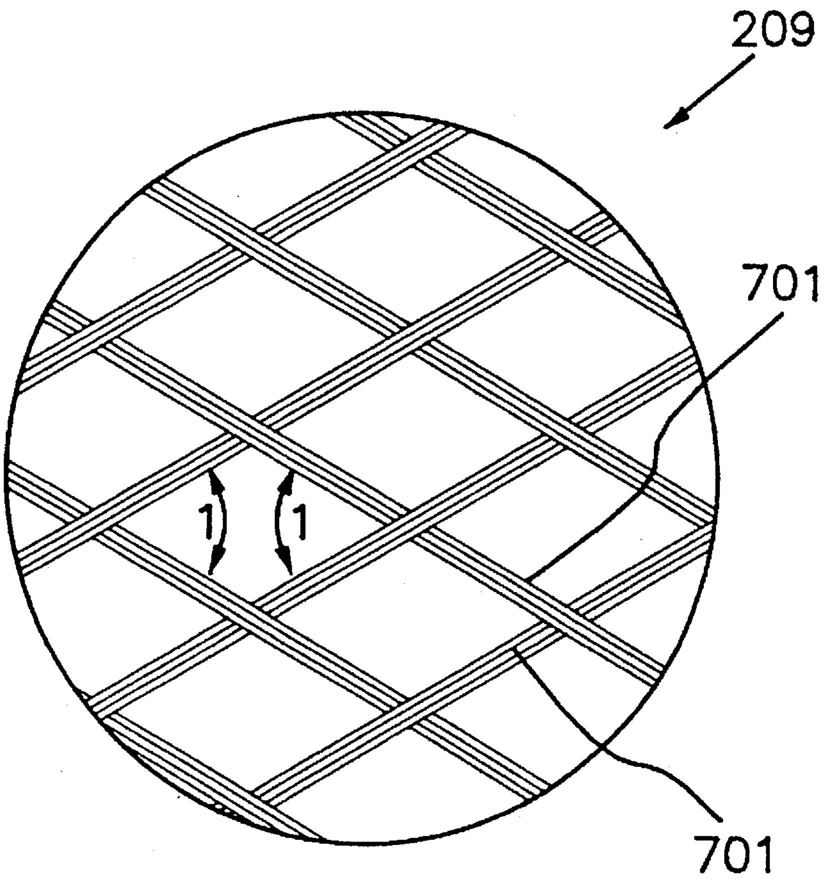
FIG. 7 is an enlarged view of the braid material used in the fetlock puller.

Referring now to FIG. 7, the preferred embodiment of braid material 209 will now be described. Depicted are flat parallel series of monofilament strands 701, such as fishing line. In the preferred embodiment, the number of monofilament strands used in each series is four but more or fewer strands could be used. Braid material 209 is constructed by loosely weaving series of strands 701 in an over and under manner as shown in FIG. 7. Braid material 209 is distinguished from a conventionally woven material in that each Angle 1 is approximately 60 degrees and the weave is loose so that series of strands 701 are in slidable relation to one another. Although 60 degrees is preferred, one skilled in the art could practice the invention with measures of Angle 1 greater than, or less than, 60 degrees. However, axial gripping is best demonstrated when Angle 1 is less than 90 degrees when braid material 209 is at rest (i.e. no traction force is being applied).

Elongated member 204 is constructed so that a line bisecting Angle 1 of braided material 209 is substantially aligned with the long axis of elongated member 204. Elongated member 204 is also constructed so that when the device is folded back, inside out, from open first end 201, the opening at the folded edge will increase in circumference to a size large enough to go over the fetlock of the particular livestock application involved. Elongated member 204 is also of sufficient length so that elongated member 204 can simultaneously be optimally positioned over foreleg 104 and grasped near second end 202 by one or more operators of the device.

Figure 3:
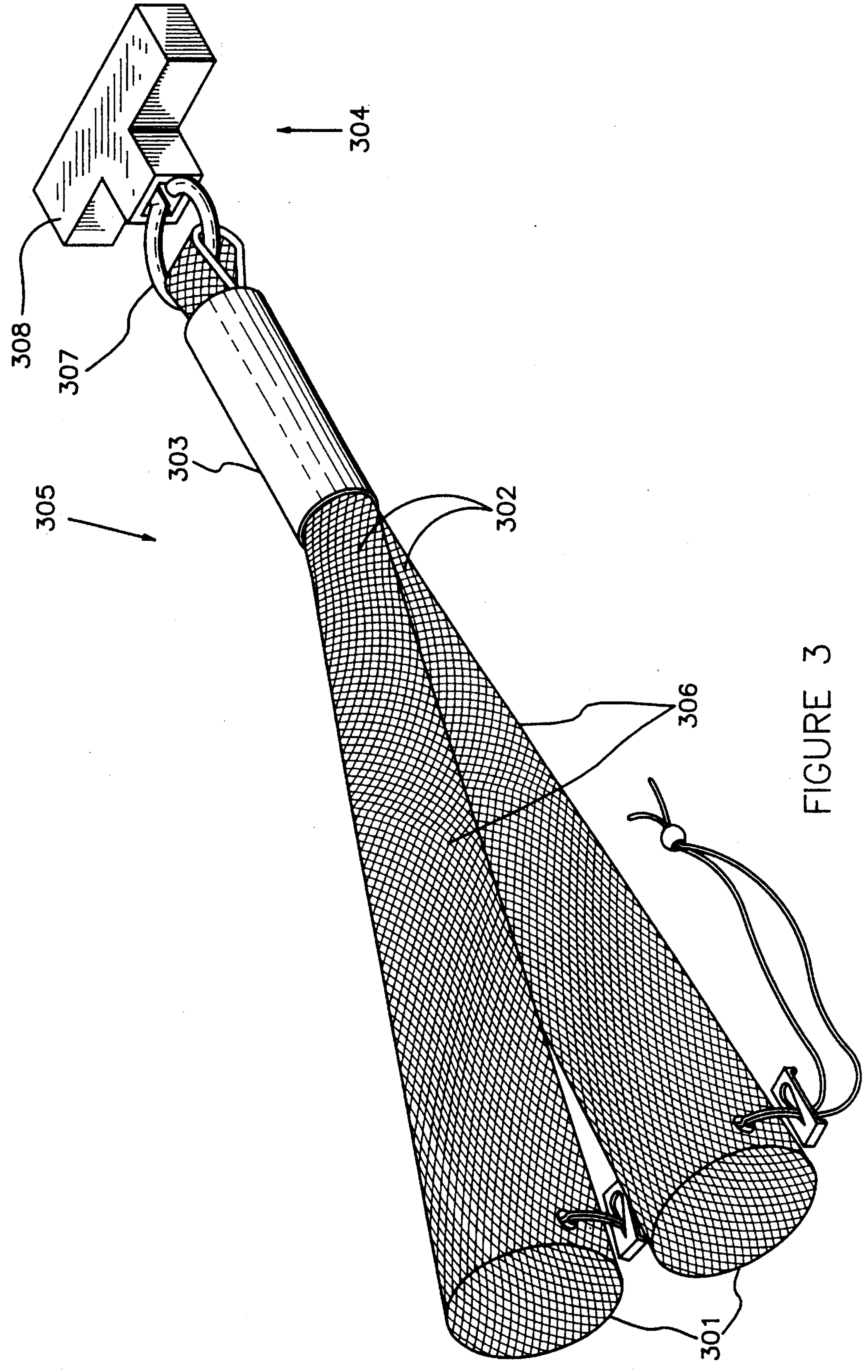
FIG. 3 is a perspective view of the paired embodiment of the invention including a T-shaped handle.

In FIG. 3 a paired embodiment of the fetlock puller is shown. In paired fetlock puller 305 open first ends 301 of elongated members 306 are each identical to open first end 201 in the single device embodiment depicted in FIG. 2. Second ends 302 of elongated members 306 are permanently connected to each other by joining means 303 and are also connected to paired attaching means 304. In the embodiment depicted, joining means 303 is formed by passing the material of each elongated member 306 through paired attaching means 304, folding the material back onto itself, and joining the folded portions to the second ends 302 with stitching and a pliable shrink-wrap. Other means for connecting paired attaching means 304 to second ends 302 could include using only stitching or only shrink-wrap, or stapling the folded portions to second ends 302, or using any other means to connect attaching means 304 to second ends 302. Metal ring 307 with T-shaped handle 308 is shown as paired attaching means 304 although, as described above for the single fetlock puller, other loops or rings could be used.

Figure 4:
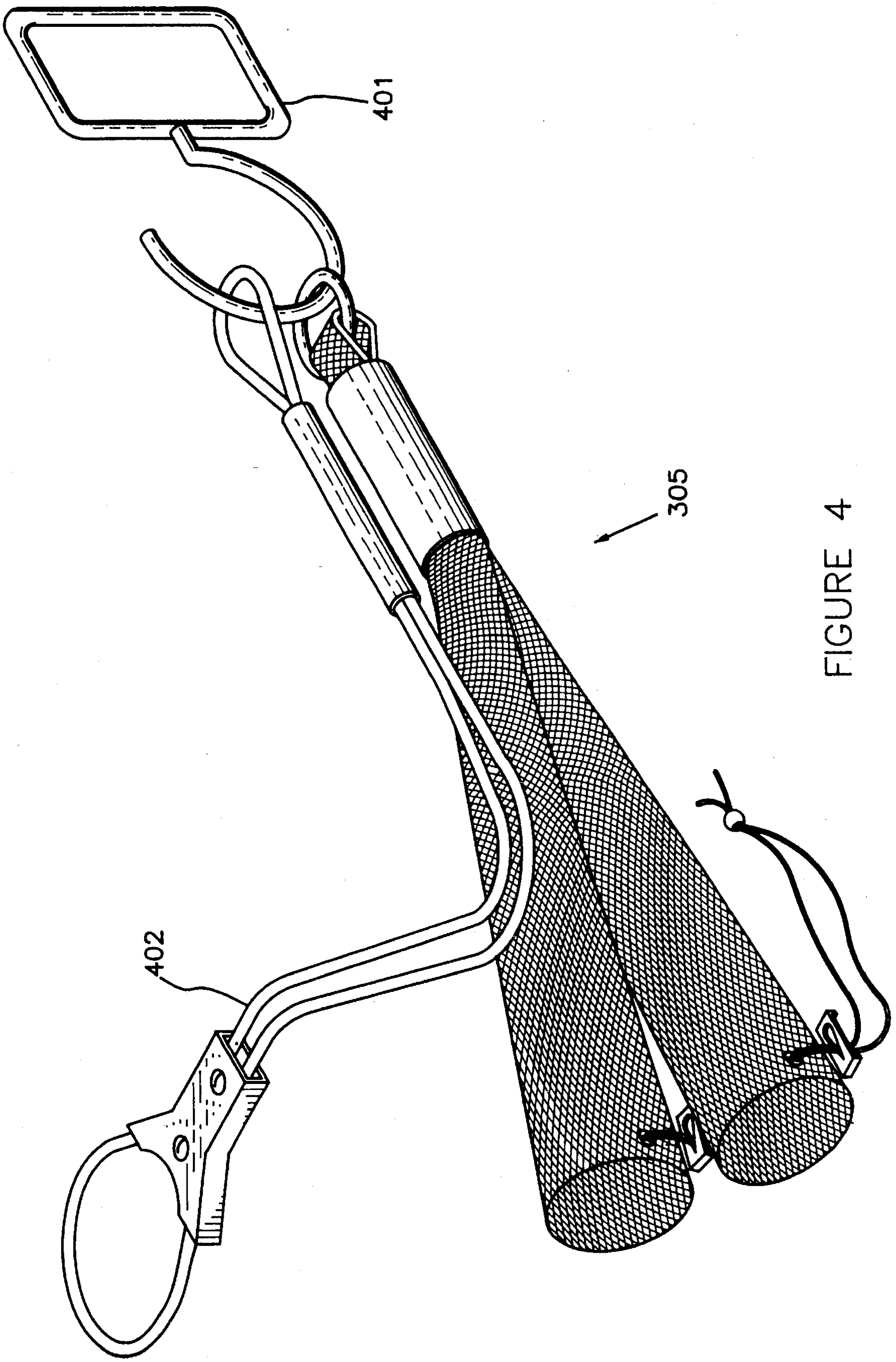
FIG. 4 is a perspective view of a paired embodiment of the invention connected, along with a cable head puller, to a loop handle.

FIG. 4 is a perspective view of paired fetlock puller 305 and cable head puller 402 attached to loop handle 401, which is one type of human traction device. Other human traction devices could be used such as a rope loop, a T-shaped handle, or any other means for connecting a metal loop to and having a place for grabbing by an operator. For mechanical traction, the configuration would be the same as that shown in FIG. 4 except a mechanical traction device, vice a human traction device, would be attached to cable head puller 402 and paired fetlock puller 305. Also, one or more single fetlock pullers 102 depicted in FIG. 2 could be connected to a human or mechanical traction device in a similar fashion.

Referring again to FIG. 5, open first end 201 is provided with tightening means 208 for tightening open first end 201 around upper foreleg portion 207 after open first end 201 has been placed over hoof 205, fetlock 206, and upper foreleg portion 207 as depicted in FIG. 2. A section of outer layer 508 is cut away to show an embodiment of tightening means

208 which includes rubber O-ring 501 and drawstring 502 disposed between inner layer 503 and outer layer 508. The two ends of drawstring 502 pass out from between inner layer 503 and outer layer 508 through aperture 504 and then pass through cinching means 505. Cinching means 505 is depicted as a flat substantially rigid member with an opening 506. After drawstring 502 is tightened, the two ends of drawstring 502 are drawn over to wedge end 507 of opening 506 and are securely wedged in place. Other cinching means, such as a simple knot or any other means for securing a string after the string has been tightened into a loop could be used.

In the embodiment shown tightening means 208 includes O-ring 501 and drawstring 502. However, other embodiments could include only an O-ring or only a drawstring as tightening means 208, or the use of looped springs, rubber or elastic bands, or any other means for decreasing the size of open first end 201. Although in the embodiment shown, O-ring 501 and drawstring 502 are disposed between inner layer 503 and outer layer 508, tightening means 208 could cooperate with open first end 201 in other ways such as weaving O-ring 501 and drawstring 502, or other similar members, through braid material 209.

Use of single fetlock puller 102 depicted in FIG. 2 is indicated if the animal fetus is in a less than ideal presentation in which one foreleg is significantly closer to the vaginal opening than the other foreleg. In operation, when the animal fetus is in this one-up, one-back presentation, a first single fetlock puller is folded back into the cocked position as depicted in FIG. 1. Although it is preferred that single fetlock puller be folded back onto itself prior to use, one skilled in the art could practice the invention by rolling elongated member 204 back from second end 202 similar to the way a condom is rolled back onto itself.

The operator removes the foreleg closest to the vaginal opening from vaginal opening 105 of the animal mother, places the first single fetlock puller over the closer foreleg, and unfolds the first single fetlock puller so as to place the first single fetlock puller in the optimal position depicted in FIG. 2. Tightening means 208 is then tightened around upper foreleg portion 207 of the closer foreleg. A traction device is then attached to the first single fetlock puller and traction is applied to this closer foreleg.

When the second foreleg becomes accessible, a second single fetlock puller is placed, and tightened, on the second foreleg using the same method used for putting on the first single fetlock puller. The second single fetlock puller is attached to a traction device together with the first single fetlock puller, and traction is applied to both forelegs. If desirable, traction may be applied simultaneously to two single fetlock pullers and to a cable head puller.

Single fetlock puller 102 may also be placed on one of the forelegs while the foreleg is still in the birth canal by simply cocking single fetlock puller 102, inserting it into vaginal opening 105, placing single fetlock puller 102 over one of the forelegs of the animal fetus, and unfolding single fetlock puller 102. The operator then tightens single fetlock puller around upper foreleg portion 207 using tightening means 208.

Paired fetlock puller 305 depicted in FIG. 3 may be used if the animal fetus is in a normal presentation in which both forelegs are relatively near one another in the birth canal. In operation, both open first ends 301 of paired fetlock puller 305 are cocked using the method described for single fetlock puller 102. The operator then removes each of the forelegs from the vaginal opening, places an open first end over each corresponding foreleg, and unfolds the body of each elongated member so that each elongated member is optimally positioned as depicted for single fetlock puller 102 in FIG. 2. The operator then tightens open first ends 301 around the upper foreleg portions of the forelegs. The operator can the apply traction using T-shaped handle 308 and or a mechanical traction device can be connected to metal ring 307. If desirable, traction may be applied simultaneously to the paired fetlock puller and to a cable head puller.

Figure 6:
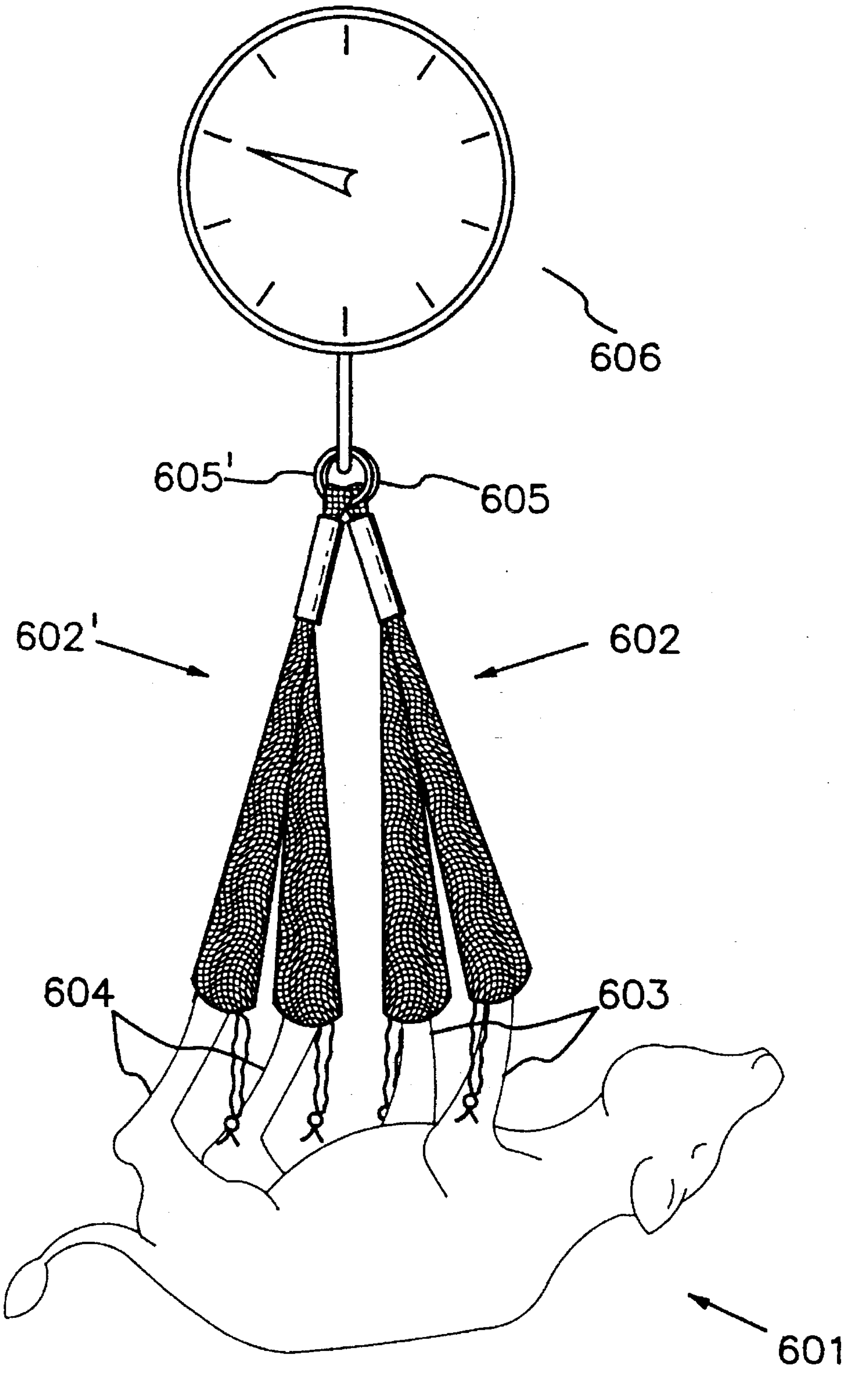
FIG. 6 shows the use of a paired embodiment of the invention for weighing a recently born animal. Two pairs are used, one pair on the forelegs and one pair on the hindlegs.

FIG. 6 shows the use of the paired embodiment of the invention for weighing newborn animal 601. Two paired fetlock puller 602 and 602' are used, paired fetlock puller 602 on forelegs 603 and paired fetlock puller 602' on hindlegs 604. In operation, to weigh newborn animal 601, the open first ends of paired fetlock pullers 602 and 602' are folded back into a cocked position just as when they are used for traction. Newborn animal 601 is subdued and paired fetlock puller 602 is placed around forelegs 603 and paired fetlock puller 602' is placed around hindlegs 604. Paired fetlock pullers 602 and 602' are then unfolded and optimally positioned as depicted in FIG. 2. Using the tightening means, the open first ends of paired fetlock pullers 602 and 602' are tightened around the upper forelegs and upper hindlegs. Attaching means 605 and 605' of paired fetlock pullers 602 and 602' are then attached to scale 606.

Although the above description is based on bovine, equine, and ovine applications, it is envisioned that one skilled in the art could adapt the invention for application to all types of animal deliveries.

There are of course other alternate embodiments which are obvious from the foregoing descriptions of the invention which are intended to be included within the scope of the invention as defined by the following claims.

I claim:

1. A device for applying traction force to the forelegs of a bovine, equine, or ovine unborn fetus or any unborn animal fetus whose legs have a hoof and fetlock, comprising:

an elongated member having an open first end and a second end connected by a passageway, said elongated member constructed of braid material comprising loosely interwoven series of fibers, said series of fibers being folded at the opening of said open first end, said series of fibers extending back toward said second end to form a double-layer of said series of fibers, said series of fibers being in slidable relation with one another to permit said elongated member to exert axial gripping forces when pulled from said second end, said open first end and said passageway sized to receive therein the foreleg of an unborn animal fetus.

2. The apparatus in claim 1 wherein said series of fibers are folded at the opening of said open first end, said series of fibers extending back substantially to said second end to form a double-layer of said series of fibers.

3. The apparatus in claim 1 or 2, further comprising a tightening means cooperating with said open first end for tightening said open first end about the fetlock and the upper foreleg portion of said foreleg at a location above said fetlock in order to initiate said axial gripping forces when said elongated member is pulled from said second end.

4. A method for applying traction force to the forelegs of a bovine, equine, or ovine unborn fetus or any unborn animal fetus whose legs have a hoof and fetlock, by the use of a fetlock puller comprising an elongated member having an open first end and a second end connected by a passageway wherein said elongated member is constructed of braid material, said open first end and said passageway sized to receive therein the foreleg of said animal fetus, and a tightening means cooperating with said open first end for tightening said open first end about said foreleg, comprising the steps of:

a) preparing at least one fetlock puller comprising an elongated member for placement over the forelegs of an unborn animal fetus;

b) cocking said fetlock puller by folding the open first end of said elongated member back onto said elongated member;

c) placing said fetlock puller over the hoof, fetlock, and upper foreleg portion of said foreleg and unfolding said fetlock puller so that said open first end of said elongated member is around said upper foreleg portion above said fetlock;

d) tightening the tightening means of said fetlock puller;

e) applying traction force at said second end; and f) delivering said animal fetus.

5. A method for weighing a bovine, equine, or ovine animal or any animal whose legs have a hoof and fetlock, by the use of a fetlock puller comprising an elongated member having an open first end and a second end connected by a passageway wherein said elongated member is constructed of braid material, said open first end and said passageway sized to therein the foreleg of said animal fetus, a tightening means cooperating with said open first end for tightening said open first end about said foreleg, and an attaching means connected to said second end, comprising the steps of:

a) preparing a plurality of fetlock pullers, each comprising an elongated member, for placement over the forelegs and hindlegs of an animal to be weighed;

b) cocking each said fetlock puller by folding the open first end of said elongated member back on to said elongated member;

c) placing said fetlock pullers over the hoof, fetlock, and upper foreleg or hindleg portion of each said foreleg and said hindleg of said animal and unfolding said fetlock puller so that said open first end of said fetlock puller is around said upper foreleg or hindleg portion above said fetlock;

d) tightening the tightening means of said fetlock puller;

e) connecting the attaching means of each said fetlock puller to a scale; and f) weighing said animal.

6. A device for applying traction force to the forelegs of a bovine, equine, or ovine unborn fetus or any unborn animal fetus whose legs have a hoof and fetlock, comprising:

a paired fetlock puller having two elongated members, each said elongated member having an open first end and a second end connected by a passageway, said elongated members constructed of braid material comprising loosely interwoven series of fibers, said series of fibers being in slidable relation with one another and said fibers being terminated at each end of said elongated member to permit said elongated members to exert axial gripping forces when pulled from said second ends, each said open first end and each said passageway sized to receive therein the foreleg of an unborn animal, said elongated members being joined to each other at said second ends; and an attaching means connected to said joined second ends such that said elongated members may be used simultaneously.

7. The apparatus in claim 6, wherein said fibers of each said elongated member are terminated at each said open first end by folding each said elongated member within the opening of each said open first end and extending said series of fibers back to each said second end to form a double-layer of said series of fibers.

8. The apparatus in claim 6, further comprising a tightening means cooperating with each said open first end of each said elongated member for tightening each said open first end about said fetlock and said upper foreleg portion at a location above said fetlock in order to initiate said axial gripping forces when said elongated members are pulled from said second ends.

9. The apparatus in claim 7, further comprising a tightening means cooperating with each said open first end of each said elongated member for tightening each said open first end about said fetlock and said upper foreleg portion at a location above said fetlock in order to initiate said axial gripping forces when said elongated members are pulled from said second ends.

* * * * *